US005701900A

United States Patent [19]
Shehada et al.

[11] Patent Number: 5,701,900
[45] Date of Patent: Dec. 30, 1997

[54] ULTRASONIC TRANSDUCER ORIENTATION SENSING AND DISPLAY APPARATUS AND METHOD

[75] Inventors: Ramez E. Shehada; Warren S. Grundfest, both of Los Angeles, Calif.

[73] Assignee: Cedars-Sinai Medical Center, Los Angeles, Calif.

[21] Appl. No.: 433,866

[22] Filed: May 1, 1995

[51] Int. Cl.⁶ .................................................. A61B 8/00
[52] U.S. Cl. .................................................. 128/662.03
[58] Field of Search ............... 128/662.03; 73/620–623; 33/343, 340, 341, 365, 366

[56] References Cited

U.S. PATENT DOCUMENTS

| | | | |
|---|---|---|---|
| 4,361,044 | 11/1982 | Kupperman et al. | 73/623 |
| 4,747,216 | 5/1988 | Kelly et al. | 33/366 |
| 5,224,467 | 7/1993 | Oku . | |
| 5,321,631 | 6/1994 | Germanetti . | |
| 5,335,663 | 8/1994 | Oakley et al. . | |
| 5,365,671 | 11/1994 | Yaniger | 33/366 |

FOREIGN PATENT DOCUMENTS

| | | |
|---|---|---|
| 61-145409 | 7/1986 | Japan . |
| 5323208 | 12/1993 | Japan . |
| 2 155 691 | 9/1985 | United Kingdom . |
| 2 211 942 | 7/1989 | United Kingdom . |

OTHER PUBLICATIONS

Ultrasound in Med. & Biol., vol. 2, Feb. 1976, p. 135, Branko Breyer.

Primary Examiner—George Manuel
Attorney, Agent, or Firm—Pretty, Schroeder & Poplawski

[57] ABSTRACT

An ultrasonic transducer orientation sensing and display apparatus, and related method, for use in providing an accurate representation of the orientation of an ultrasonic transducer's imaging plane. The orientation sensing and display apparatus includes an ultrasonic transducer having an integral orientation sensor, a processor, and a display. The representation of the imaging plane as indicated on the display is based on electrical signals generated by the orientation sensor. The ultrasonic transducer, in accordance with one embodiment of the present invention, is integrated near the distal end or tip of an elongated tube of a laparoscopic instrument used for ultrasonic imaging. The orientation sensor is a biaxial gravitational sensor, composed of two orthogonal sensing toroids to sense rotation about any axis lying in a horizontal plane. Each sensing toroid has a hollow tubular shape that contains a gravity indicator that is free to move within the respective sensing toroid for measuring rotation about an axis through the toroid's center. Gravity causes each gravity indicator to migrate to the lowest portion of the respective toroid. The orientation also can include a permanent magnet thus providing a tri-axial sensor.

28 Claims, 10 Drawing Sheets

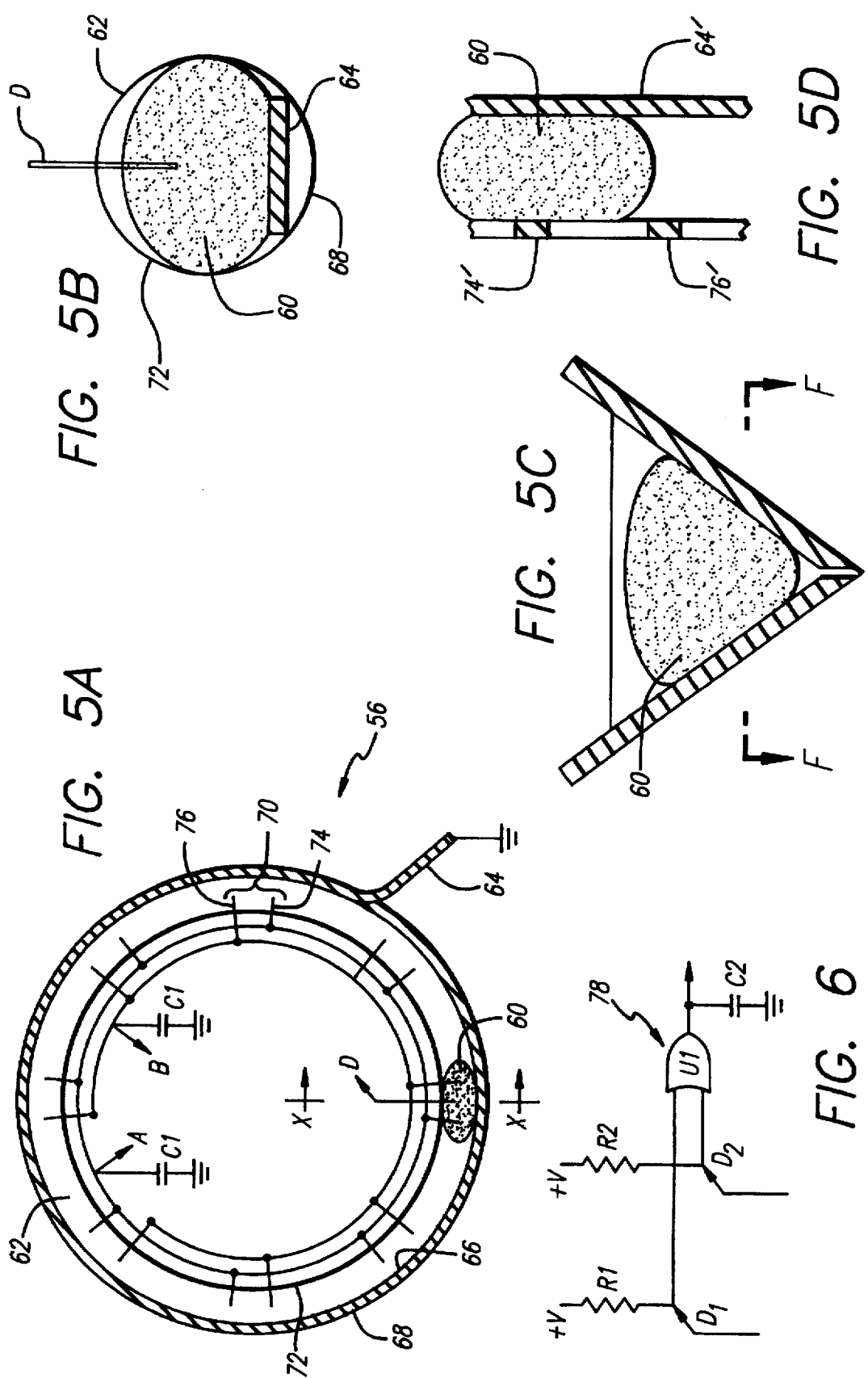

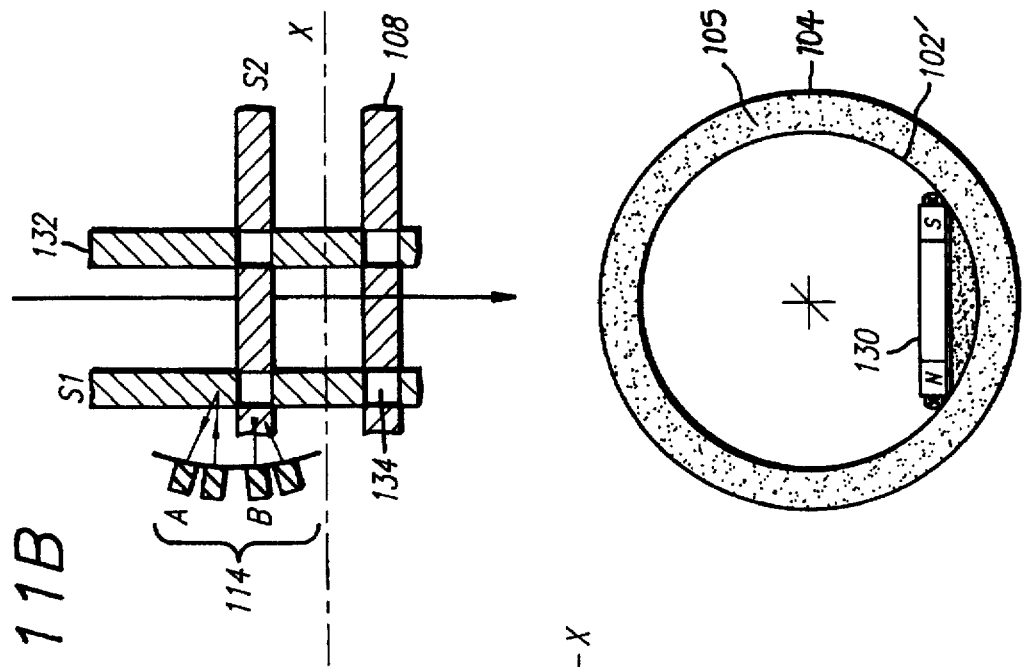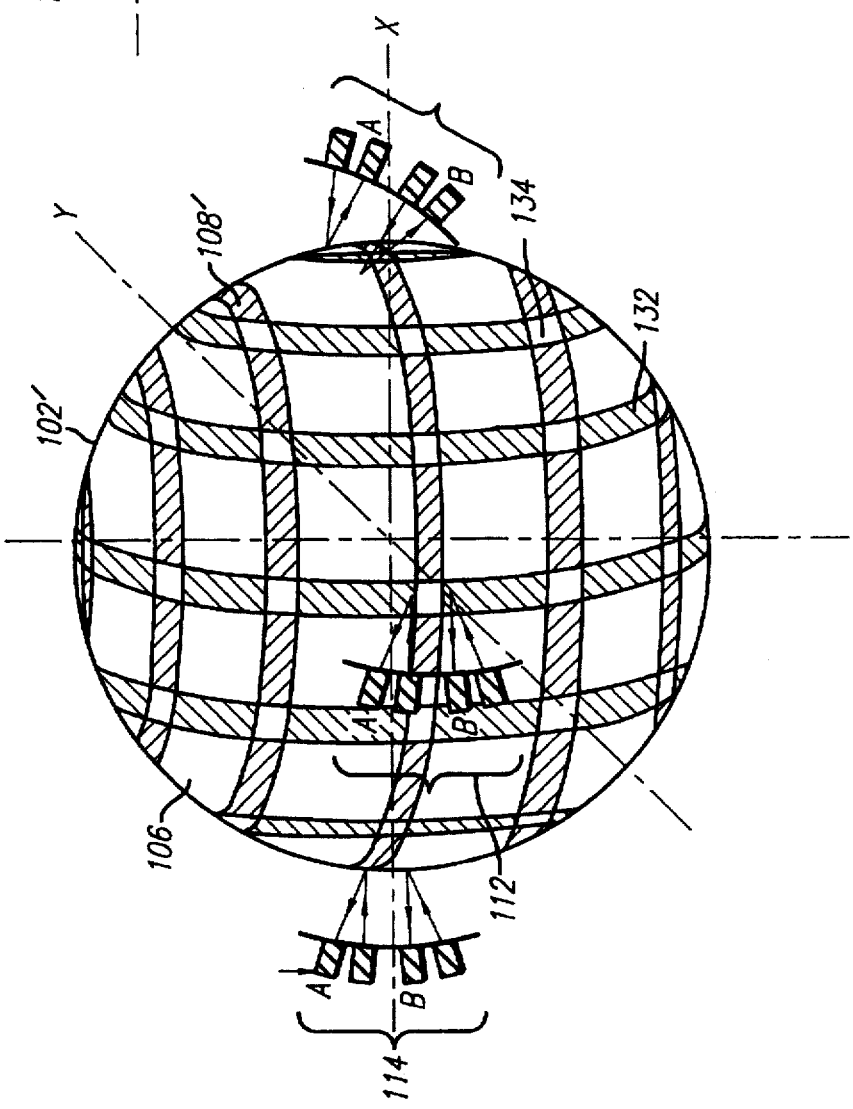

ULTRASONIC TRANSDUCER ORIENTATION SENSING AND DISPLAY APPARATUS AND METHOD

BACKGROUND OF THE INVENTION

This invention relates generally to ultrasonic imaging and, more particularly, to the definition of the imaging plane of an ultrasonic image using an orientation sensor.

Ultrasonic imaging using a linear transducer array provides information regarding the interior of a body or an organ in an imaging plane. Typically, an ultrasonic sensor is placed in contact with the skin and ultrasonic waves are directed from the transducer array into the body in an imaging plane. Scattered waves from the structure within the body are collected by the transducer array and the resulting electrical signals are processed to produce an image. More recently, laparoscopic ultrasonic imaging or sonography has been developed that allows probing into the interior of the body through a small incision cut in the skin. The tip of the laparoscope that has the transducer array is invisible to the laparoscope's operator once it is inserted into the body.

Although a video laparoscope, which often accompanies the ultrasonic imaging laparoscope, can provide a visual indication of the tip's orientation, the tip, when inside the body, can be obscured by organs or the like. This is especially a concern for an ultrasonic imaging laparoscope that has an articulated tip, i.e., a short tube section that extends past a flexible pivot-like tube section and that can be maneuvered in almost any direction through external controls. The articulated tip is useful for imaging the backside of an organ or the like. Thus, if the operator loses the orientation of the laparoscope's imaging plane with respect to the surrounding anatomy because the articulated tip is obscured from view, the operator loses the ability to accurately determine the direction of the imaging plane. Accordingly, the operator loses the ability to locate hidden structures of interest (e.g., tumors, ducts, etc.) for diagnosis or surgical intervention. Since the main purpose of laparoscopic ultrasonic imaging is to locate and observe hidden structures, it is desirable for the operator to have the ability to accurately determine the imaging plane.

General to most ultrasonic imaging systems is a feature that allows the operator, when recording a desired ultrasonic image, to indicate the source of the image. More particularly, the operator can place a special cursor, representing the image plane of the transducer, over a body pattern to show the imaging plane's orientation with respect to a patient's body. However, any movement of the ultrasonic transducer's orientation, with respect to the body, changes the orientation of the imaging plane and therefore requires the operator to readjust the special cursor.

Accordingly, there is a need for a ultrasonic transducer orientation sensing and display apparatus that provides a user with an accurate representation of the orientation of the transducer's imaging plane. Further, there is a need for an apparatus that automatically orients a special cursor in response to movement of the laparoscope's imaging plane to accurately describe the orientation of the imaging plane with respect to a patient's body. The present invention satisfies these needs.

SUMMARY OF THE INVENTION

The present invention is embodied in an apparatus for providing an indication of the imaging plane of an ultrasonic transducer, comprising a gravitational sensor, a display, and a processor. The gravitational sensor provides an orientation signal representing the spatial orientation of the ultrasonic transducer. The display provides a visual representation of the image plane and the processor, associated with the gravitational sensor and the display, processes the orientation signal and generates a display signal that causes the display to provide the visual representation of the image plane.

In a more detailed feature of the present invention, the gravitational sensor has two orthogonal sensing toroids. Each toroid includes a plurality of electrode units uniformly spaced apart around the toroid, a common electrode, and a gravity indicator. The gravity indicator freely moves within the toroid such that the gravity indicator tends towards the portion of the toroid at the lowest gravity potential. The gravity indicator, as it moves to the toroid's lowest gravity potential, provides electrical contact between the common electrode and the electrodes units. Thus, the gravity indicator provides an orientation signal as it passes the respective electrode unit.

The gravity indicator may be a droplet of mercury metal or a ball formed of a nontoxic material.

In another embodiment of the present invention, a gravity sensor provides an orientation signal compatible with a computer mouse input port. The gravity sensor includes a gravity indicator responsive to gravity and a plurality of probe pairs. The probe pairs monitor the movement of the gravity indicator about an axis. Each probe pair provides first and second pulse signals. The timing between the pulse signals provides an indication of the angle and direction of the gravity indicator's movement.

Other features and advantages of the present invention should become apparent from the following description of the preferred embodiments, taken in conjunction with the accompanying drawings, which illustrate, by way of example, the principals of the invention.

BRIEF DESCRIPTION OF THE DRAWINGS

FIG. 5A is a cross-sectional elevational view of a sensing toroid of FIG. 4, showing the electrode configuration within the sensing toroid.

FIG. 5B is a cross-sectional view, taken along the line X—X of FIG. 5A, showing the electrode configuration within the sensing toroid.

FIG. 5C is a cross-sectional view showing the electrode configuration of an alternative embodiment of a sensing toroid of the present invention.

FIG. 5D is a cross-sectional view, taken along the line F—F of FIG. 5C, showing the electrode configuration within the sensing toroid.

FIG. 6 is a schematic diagram of a reference position circuit for indicating a predetermined reference orientation of the biaxial sensor shown in FIG. 4.

FIG. 11A is a perspective view of a tri-axial spherical orientation sensor that includes a suspended spherical ball having orthogonal reflective stripes to determine an orientation about three axes.

FIG. 11B is a more detailed view of a selected area of the spherical ball shown in FIG. 11A.

FIG. 11C is a cross-sectional view of the spherical ball of FIG. 11A, showing a permanent magnet located within the spherical ball.

DESCRIPTION OF THE PREFERRED EMBODIMENTS

Figure 1:
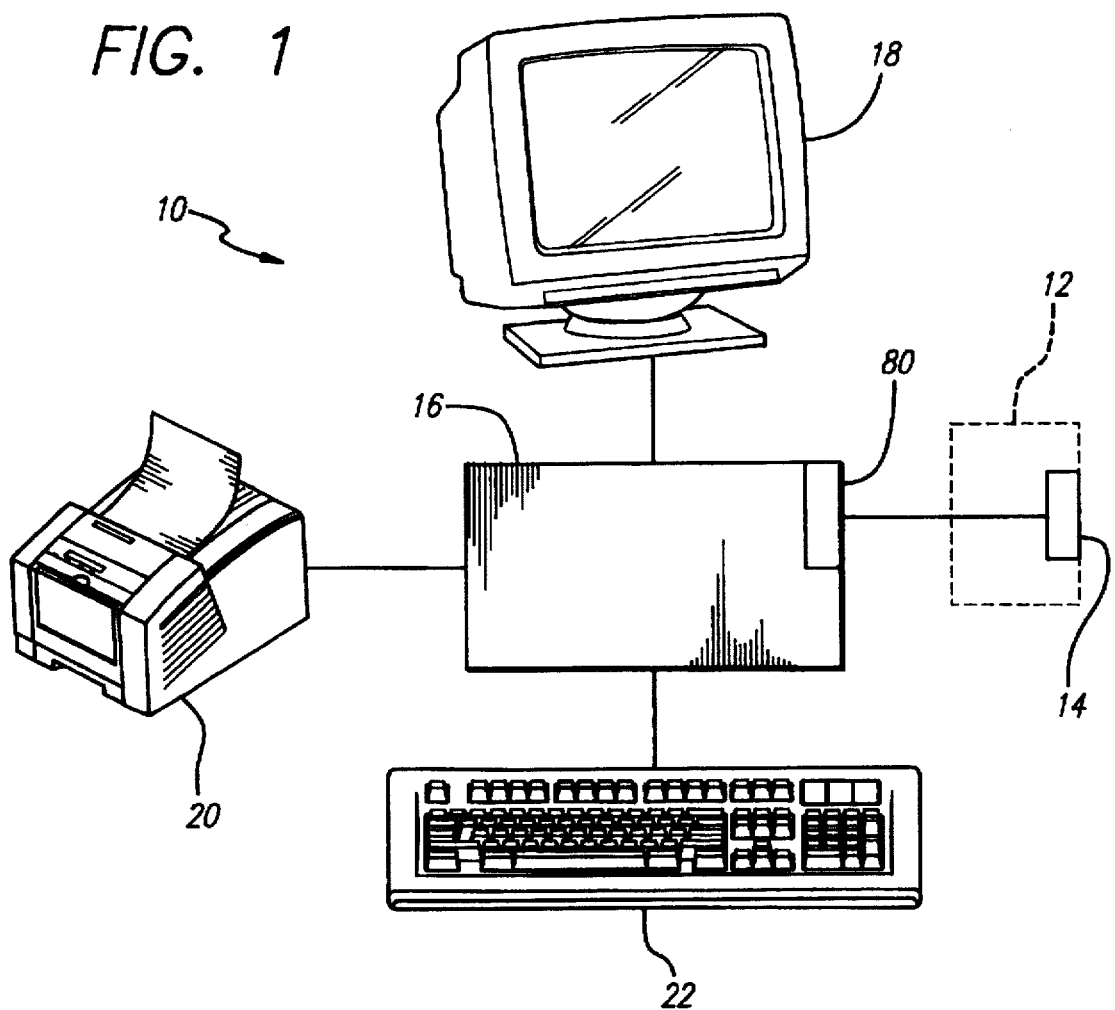
FIG. 1 is a block diagram of an ultrasonic transducer orientation sensing and display apparatus of the present invention.

As shown in the exemplary drawings, and particularly in FIG. 1, the present invention is embodied in an ultrasonic transducer orientation sensing and display apparatus 10, and related method, for use in providing an accurate representation of the orientation of an ultrasonic transducer's imaging plane. The orientation sensing and display apparatus includes an ultrasonic transducer 12 having an integral orientation sensor 14, a processor 16, a display 18, a printer 20 and a keyboard 22. The representation of the imaging plane as indicated on the display is based on electrical signals generated by the orientation sensor.

Figure 2:
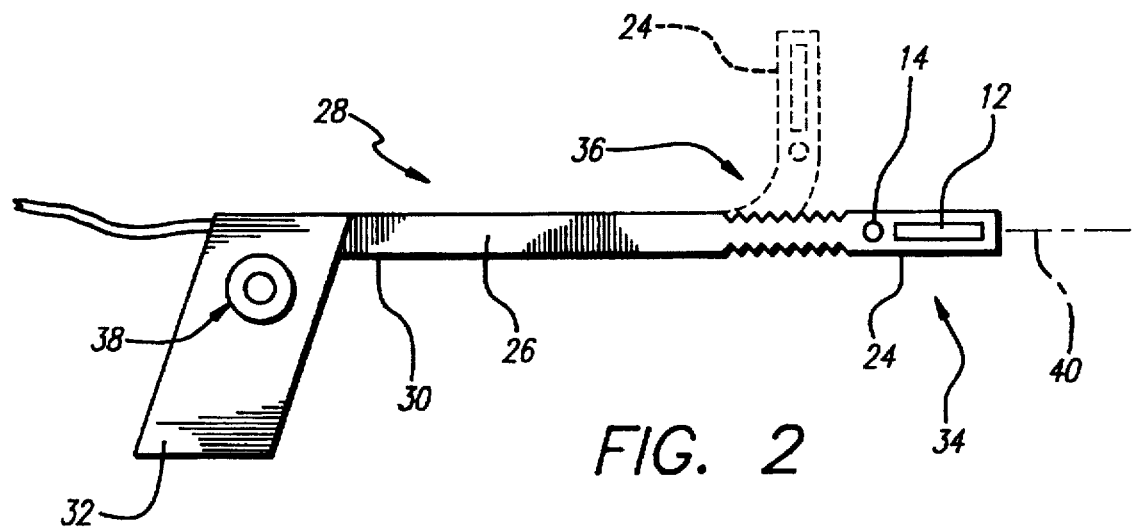
FIG. 2 is an elevation view of a laparoscopic instrument, in accordance with the present invention, having an elongated tube that houses an ultrasonic transducer and an orientation sensor.

The ultrasonic transducer 12, in accordance with one embodiment of the present invention, shown in FIG. 2, is integrated near the distal end 24 or tip of an elongated tube 26 of a laparoscopic instrument 28. The elongated tube is inserted into a body cavity through a small incision cut in the skin. At the proximal end 30 of the elongated tube is connected to a handle 32 for orienting the ultrasonic transducer. Preferably, the instrument's distal end has a short tube section 34 that can be articulated about a pivot-like region 36 using mechanisms 38 included near the instrument's handle. The orientation sensor 14 and the ultrasonic transducer are housed within the short tube section 34.

The ultrasonic transducer 12 typically includes a linear array (not shown) that is aligned along an axis [40] through the center of the short tube section 34 [elongated tube 26]. The array scans in an imaging plane perpendicular to the linear array. The short tube section's [elongated tube's] axis lies in the imaging plane. The imaging plane is rotated about an [the tube's] axis 40 of the elongated tube 26 by rotating the short tube section, and thus the linear array, about the elongated tube's axis.

Figure 3:
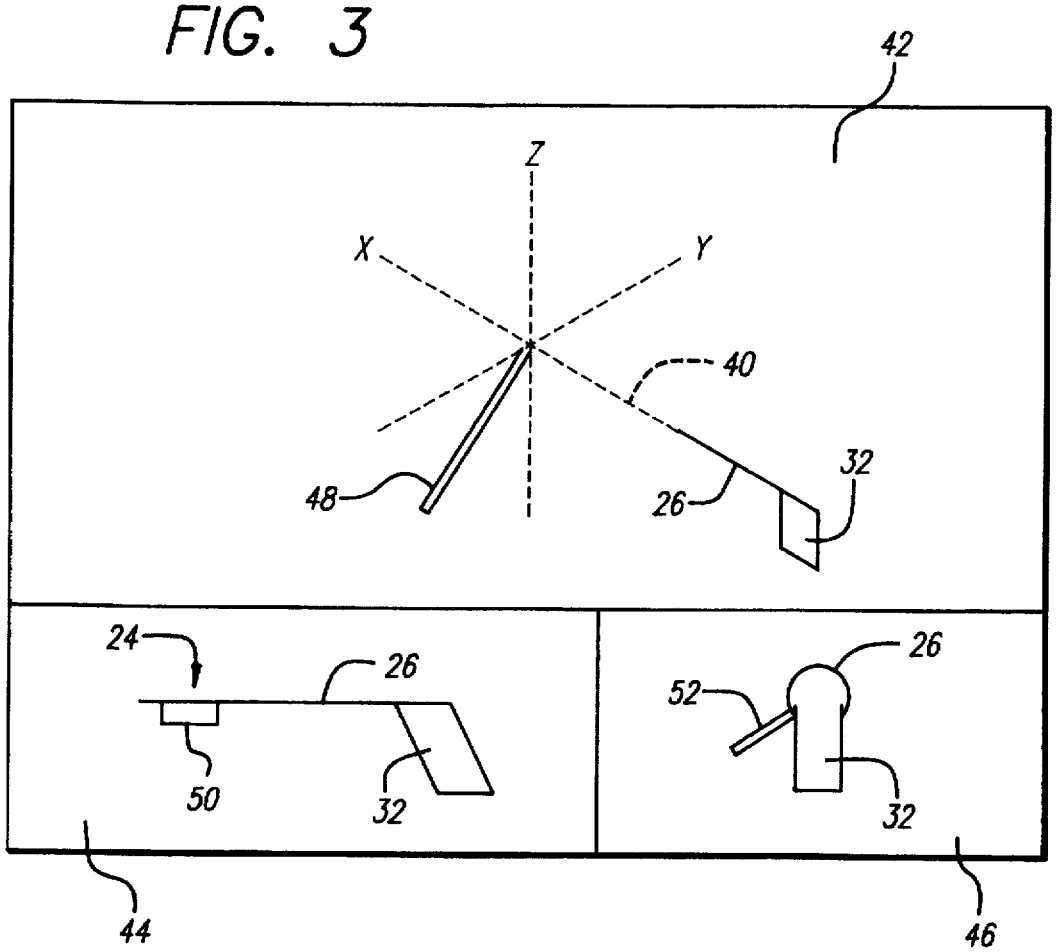
FIG. 3 is a schematic representation of a display indicating an imaging plane, as related to a handle of an ultrasonic laparoscopic instrument, generated by the orientation sensing and display apparatus of FIG. 1.

The processor 16 is an IBM PC compatible computer having a high resolution VGA display 18. As shown in FIG. 3, the imaging plane, with respect to the laparoscopic instrument's handle 32, is indicated on the display. The display is divided into three views, one three-dimensional view 42 and two two-dimensional views 44 and 46. Each view contains a stationary element, that indicates the instrument's handle and elongated tube 26, and a dynamic element that indicates the position of articulated tip 24 and/or the imaging plane.

More particularly, the first view 42 is a three-dimensional view located in the upper middle portion of the display 18. The axis 40 of the elongated tube 26 is shown aligned with an x axis and perpendicular to orthogonal y and z axes. A vector 48 radiating from an origin of the x, y, and z axes represents the imaging direction. The vector and the axis of the short articulated tube section (not shown) define the imaging plane.

The second view 44 is a two-dimensional side view located in the lower-left portion of the display 18. This view shows the orientation of the articulated tip 24 and a rectangular element 50 that indicates the orientation of the imaging plane. Since the imaging plane is represented in only two dimensions, different colors can be used to further indicate the orientation of the imaging plane. For example, a yellow color indicates that the imaging plane shown in the rectangular element lies in the x-z plane, a blue color indicates that the imaging plane extends into the plane of the display 18, and a red color indicates that the plane extends out from the plane of the display.

In the lower-right portion of the display 18 is a rear view 46 of the instrument showing the handle 32 and the elongated tube 26. The imaging plane is shown as a vector 52 that extends from the axis 40 of the elongated tube.

Figure 4:
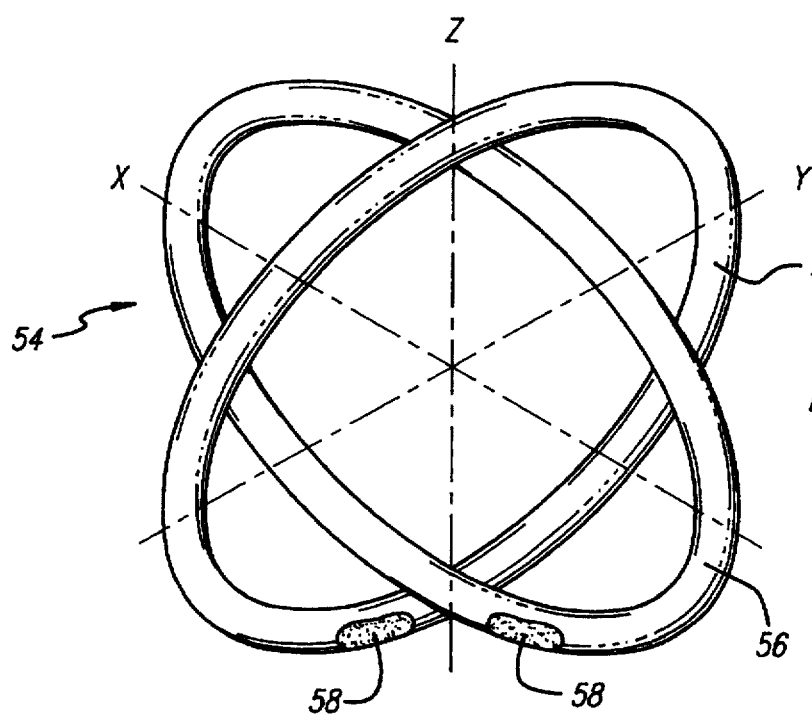
FIG. 4 is a perspective view of a biaxial orientation sensor of the present invention, comprising two orthogonal hollow sensing toroids that each contain a gravity indicator.

In one embodiment of the present invention, shown in FIG. 4, the orientation sensor 14 is a biaxial gravitational sensor 54, composed of two orthogonal sensing toroids 56 to sense rotation about any axis lying in a horizontal plane. Each sensing toroid has a hollow tubular shape that contains a gravity indicator 58 that is free to move within the respective sensing toroid for measuring rotation about an axis through the toroid's center. Gravity causes each gravity indicator to migrate to the lowest portion of the respective toroid. The relative positions of the gravity indicators within the two toroids of the biaxial sensor define a position on the surface of an imaginary sphere centered about the x, y and z axes.

A further description of each sensing toroid 56 of the biaxial sensor 54 is shown in FIGS. 5A–5D. The sensing toroid has a glass tube 62 with a common electrode 64 extending along the interior surface 66 of the toroid's outer wall 68. The toroid also has several electrode units 70 that are spaced at predetermined intervals along the toroid's inner wall 72. Each electrode unit has two spaced apart sensing or signal electrodes 74 and 76 that protrude into the space enclosed by the hollow toroid. One signal electrode 74 of each electrode unit is designated as electrode A and the other signal electrode 76 is designated as electrode B. Electrode A in each electrode unit is spaced away, in a clockwise direction, from the corresponding electrode B. All of the electrodes designated as electrode A are connected together in parallel and all of the electrodes designated as electrode B are connected together in parallel. The number, and hence the angular spacing, of electrode units determines the sensor's resolution.

The gravity indicator 60 is shown as a small drop of mercury. The mercury must be sufficiently small so that it cannot make contact between the signal electrodes 74 and 76 of two adjacent electrode units 70, but must be sufficiently large to provide contact between the signal electrodes of a given electrode unit.

Each sensing toroid 56 produces electrical pulses on signal lines A and B. The electrical pulses on line A are produced when the gravity indictor 60 contacts any signal electrodes designated as electrode A, thus providing an electrical path from line A to the common electrode 64, and the electrical pulses on line B are similarly produced when the gravity indicator contacts any signal electrode B. Two capacitors C1, in the range of 0.01 to 0.1 microfarads, are connected between lines A and B and a ground terminal to reduce the sensor's susceptibility to electrical noise.

Figure 7A:
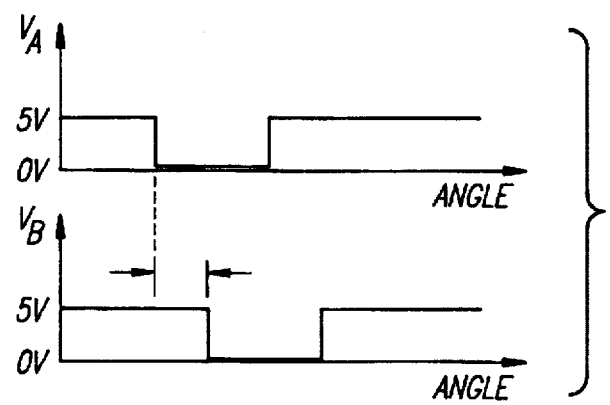
FIG. 7A is a graph showing the timing relationship between electrical signals on the sensing electrodes of the sensing toroid of FIG. 5A, when a gravity indicator within the sensing toroid is moving in a counterclockwise direction.
Figure 7B:
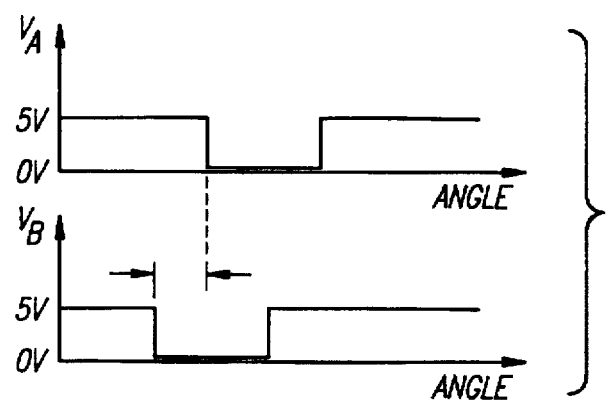
FIG. 7B is a graph showing the timing relationship between electrical signals on sensing electrodes of the sensing toroid of FIG. 5A, when the gravity indicator within the sensing toroid is moving in a clockwise direction.

Since the angular spacing between the electrode units 70 is defined, the electrical pulses provide a series of pulses, that are counted by the processor 16, representing the angular rotation of the sensing toroid about a horizonal axis. The direction of the angular rotation is given by the relative time delay between the pulses on lines A and B, as shown in FIGS. 7A and 7B. This time delay is produced by the spacing between the signal electrodes A and B of a given electrode unit. Since the gravity indicator 60, as it comes into contact with an electrode unit, will contact one signal electrode before the other signal electrode, the time delay between the pulses on lines A and B indicates the direction of rotation. Thus, if the sensing toroid 56 is rotating in a clockwise direction, gravity causes the gravity indicator to rotate in a counterclockwise direction as it approaches an electrode unit. The gravity indicator first connects electrode A to the common electrode 64, causing the voltage on the line A to drop to a low state. Then, as the gravity indicator rotates further, it connects electrode B, in addition to electrode A, to the common electrode. After further rotation, the gravity indicator connects only the electrode B connection to the common electrode. Accordingly, as shown in FIG. 7A, the voltage $V_A$ on line A leads the voltage $V_B$ on line B. Likewise, as shown in FIG. 7B, if the gravity indicator is rotating in a clockwise direction, the voltage $V_A$ on line A lags the voltage $V_B$ on line B.

The sensing toroid 56 may further include a reference electrode D (FIGS. 5A and 5B) that is used to calibrate the orientation sensor 14 to a known orientation. For example, during the first moments of operation of the orientation sensor, the position of the gravity indicator 60 is undefined since the electrical signals on lines A and B can be produced by any electrode unit 70. Further, the processor 16 may miss a count or incorrectly indicate a rotational direction. However, when the gravity indicator contacts the reference electrode D within its associated sensing toroid 56, the location of the gravity indicator within the sensing toroid is then defined.

A logic circuit 78 for indicating when the gravity indicators 60 of both sensing toroids 56 are simultaneously in contact with the respective reference electrodes D is shown in FIG. 6. A signal is sent from the logic circuit to the processor 16 to recalibrate the orientation direction indicated on the display 18. The logic circuit includes an OR gate U1 and two resistors R1 and R2, respectively, that are connected between a voltage source V+ and one of the input terminals of the OR gate. The resistors preferably have a resistance between 1 and 5 kilohms. One input terminal of the OR gate is connected to the reference electrode D of one sensing toroid 56 and the other input terminal is connected to the other reference electrode D of the other sensing toroid. A capacitor C2 on the output terminal of the OR gate suppresses noise glitches.

The cross-sectional shape of the sensing toroids 56 and the electrode units 70 can have a variety of configurations. For example, as shown in FIG. 5B, the sensing toroid can be a glass tube 62 and the common electrode 64 can be a flat conductive stripe that encompasses the interior of the toroid and that lies against the interior surface 66 of the toroid's outer wall 68. The signal electrodes 74 and 76 and the reference electrode D can be thin pin-like probes that protrude a predetermined distance toward the interior of the sensing toroid in a radial direction originating from the toroid's center. Alternatively, as shown in FIGS. 5C and 5D, the toroid can have a triangular cross-section with the common electrode 64' being a uniform continuous electrode along one side of the triangular inner surface and the signal electrodes 74' and 76' placed in insulated pairs along the opposite side of the toroid's triangular inner surface.

The electrical signals generated by the biaxial sensor 54 (FIGS. 4 and 5A) preferably are connected to the mouse port 80 (FIG. 1) of the processor 16 or through an RS-232 serial input/output port, which has been configured as a mouse interface. The mouse interface has two input lines for an x-movement channel input, two input lines for a y-movement channel input, a right-button channel input line, and a left-button channel input line. The lines A and B of the first toroid sensor 56 of the biaxial sensor are connected to the two input lines of the x-movement channel input and the lines A and B of the second toroid sensor are connected to the two input lines of the y-movement channel input. The output of the logic circuit 78 is connected to the right-button channel input line. An operator's reference push button switch (not shown), that allows the operator to mark a certain orientation for future reference, is connected to the left-button channel input line.

Figure 10:
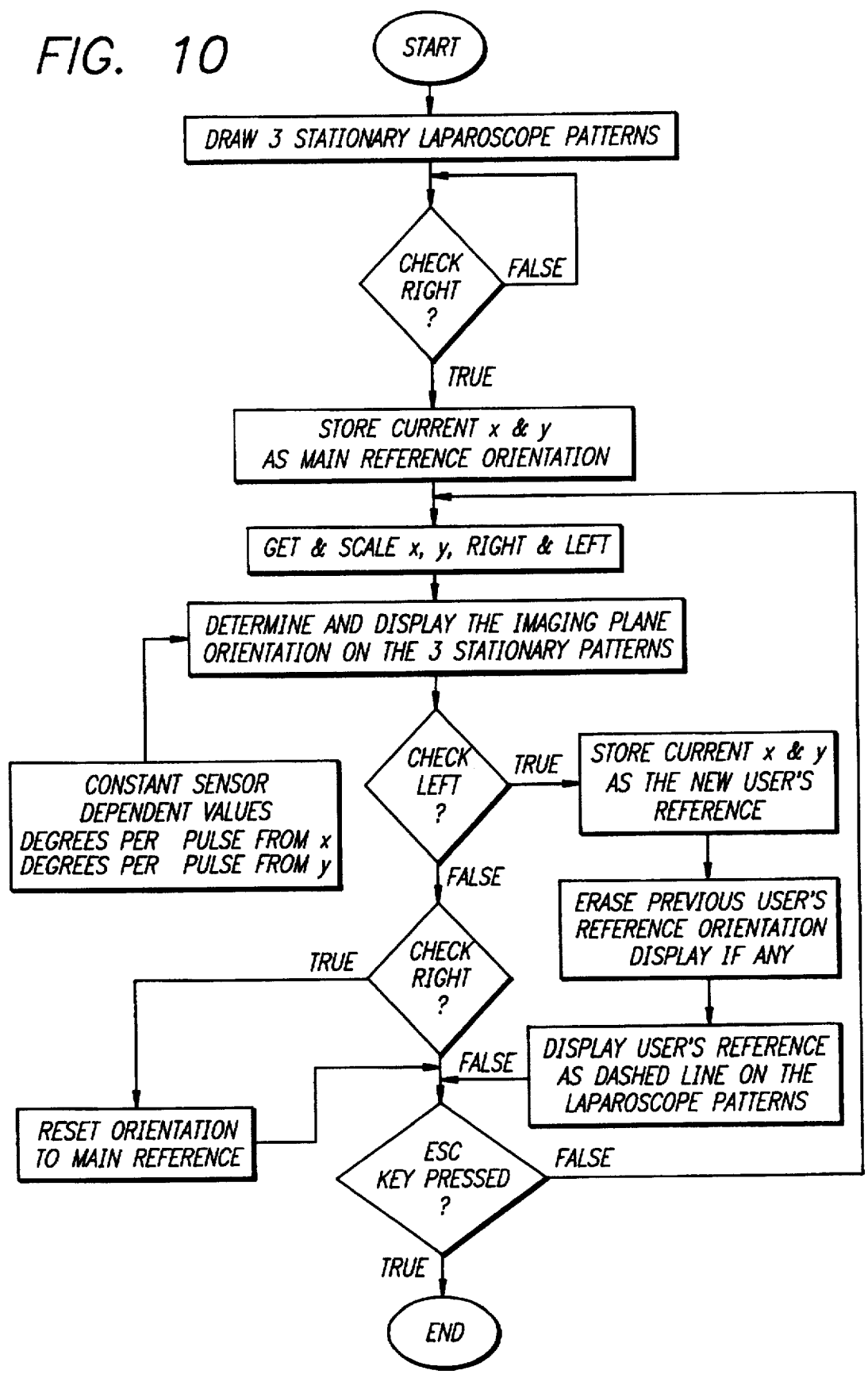
FIG. 10 is a flow chart indicating the process used by the processor and its associated software to determine and display the orientation of the ultrasonic transducer's imaging plane.

A flow chart of the software used to convert the electrical signals received at the mouse port 80 to the views 42–46 on the display 18, is shown in FIG. 10. The first step is to draw three stationary laparoscope patterns. The processor 16 then checks the channel input value associated with the right-button channel input line. If there is no signal, the software loops back in a repetitive loop until a true signal is received.

When a true signal is received, the processor then stores the current x and y values as a main reference orientation. The x and y values are converted to numerical values by the mouse interface software provided by the operating system of the processor. The processor then gets from the mouse interface software, the x and y values and the left and right-button values which may have changed during an intervening time period. Based on predetermined values determined by the orientation sensor's design, the processor determines and displays the imaging plane's orientation on the three views 42–46.

For example, the sensing toroid 56 shown in FIG. 5A indicates a rotation of 45° per pulse signal pair from an electrode unit 70. The processor 16 then checks the status of the left channel input line. If the left-button channel input line is true, the processor stores the current x and y values as a user reference and erases any previous user's reference. The processor then indicates on the display 18 the new user's reference as a dash line on the laparoscope pattern. If the left-button channel input line is false, the processor then checks the right-button channel input line. If the right-button channel input line is true, the processor resets the orientation sensor's main reference orientation. Finally, the processor checks whether the escape key, for ending the program, has been pressed on the keyboard 22. If the escape key has not been pressed, the processor loops back to again retrieve the x-movement, y-movement, right-button and left-button channel input values.

Thus, using currently available processors, such as an IBM PC compatible computer having readily available mouse interface software, the orientation sensor 14, and associated display software, provide an operator with an indication of the ultrasonic transducer's orientation in a horizontal plane.

Figure 8B:
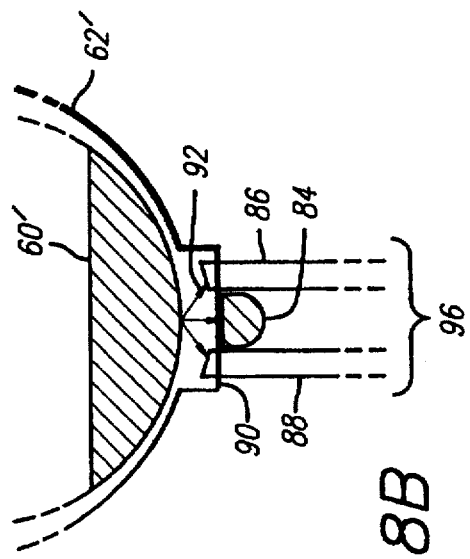
FIG. 8B is a cross-sectional view, taken along line X—X of FIG. 8A, showing the optical fiber configuration of the sensing toroid of FIG. 8A.
Figure 8C:
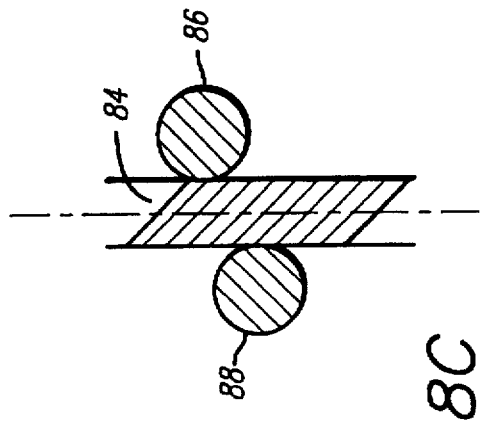
FIG. 8C is a top cross-sectional view, showing the optical fiber configuration of the sensing toroid of FIGS. 8A and 8B.
Figure 8A:
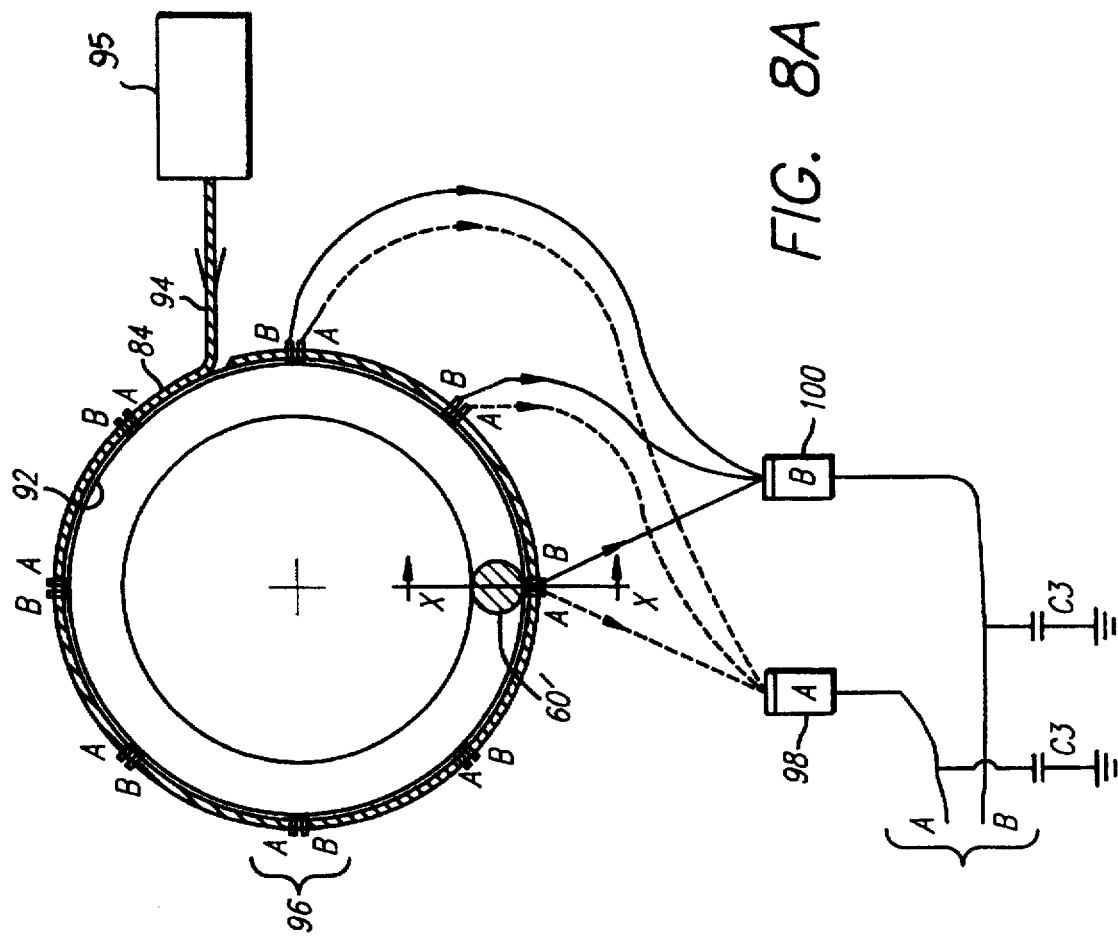
FIG. 8A is a cross-sectional elevational view of another embodiment of a sensing toroid of the present invention, with a schematic representation of optical fibers and associated photosensors for generating electrical signals representing the orientation of the sensing toroid.

An alternative embodiment of the orientation sensor is shown in FIG. 8A–8C. In this embodiment, optical fibers, instead of signal electrodes, monitor the position of a gravity indicator 60'. The gravity indicator is a shiny ball that reflects light from an illumination fiber 84 to a pair of detection fibers 86 and 88. The shiny ball preferably is formed of stainless steel or other nontoxic reflective material.

The illumination fiber 84 encompasses the toroid's exterior surface 90 and has a "leaky" surface 92, prepared using sandpaper, that is directed towards the interior of the toroid. Illumination light, from a light source 95, is guided through an intact portion 94 of the illumination fiber to the "leaky" surface, where it escapes the fiber to illuminate the interior of the sensing toroid. The two detection optical fibers 86 and 88, are placed on either side of the illumination fiber to form an optical unit 96. Similar to the signal electrodes 74 and 76 mentioned above (FIG. 5A), one detection optical fiber 86 is associated with voltage signal A and the other detection optical fiber 88, offset from the other detection optional fiber 86, is associated with a voltage signal B. The detection optical fibers of each optical unit are respectively connected to photodetectors 98 and 100.

The photodetectors 98 and 100 convert light pulses to electrical pulse signals on lines A and B, respectively. Two capacitors C3, preferably having a capacitance in the range of 0.01 to 0.1 microfarads, are connected between the lines A and B, respectively, and the ground terminal.

Figure 9B:
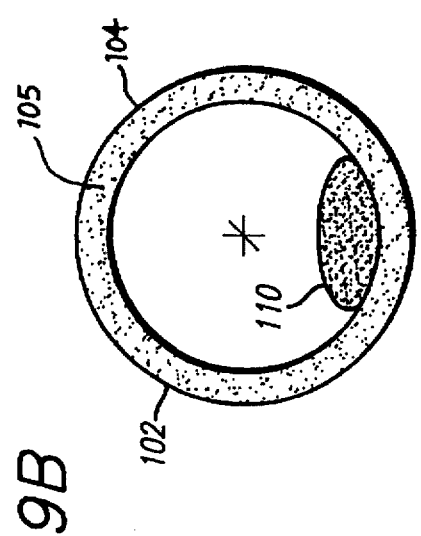
FIG. 9B is a cross-sectioned view of the suspended spherical ball shown in FIG. 9A.
Figure 9C:
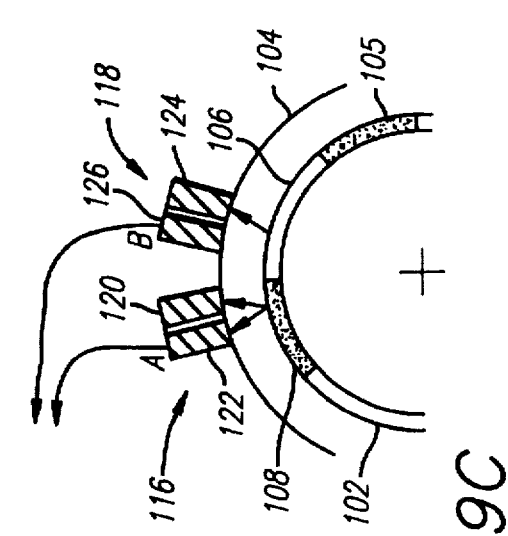
FIG. 9C is a side cross-sectional view indicating the orientation of an optical unit pair for detecting the rotation of the suspended spherical ball about an x axis or a y axis.
Figure 9A:
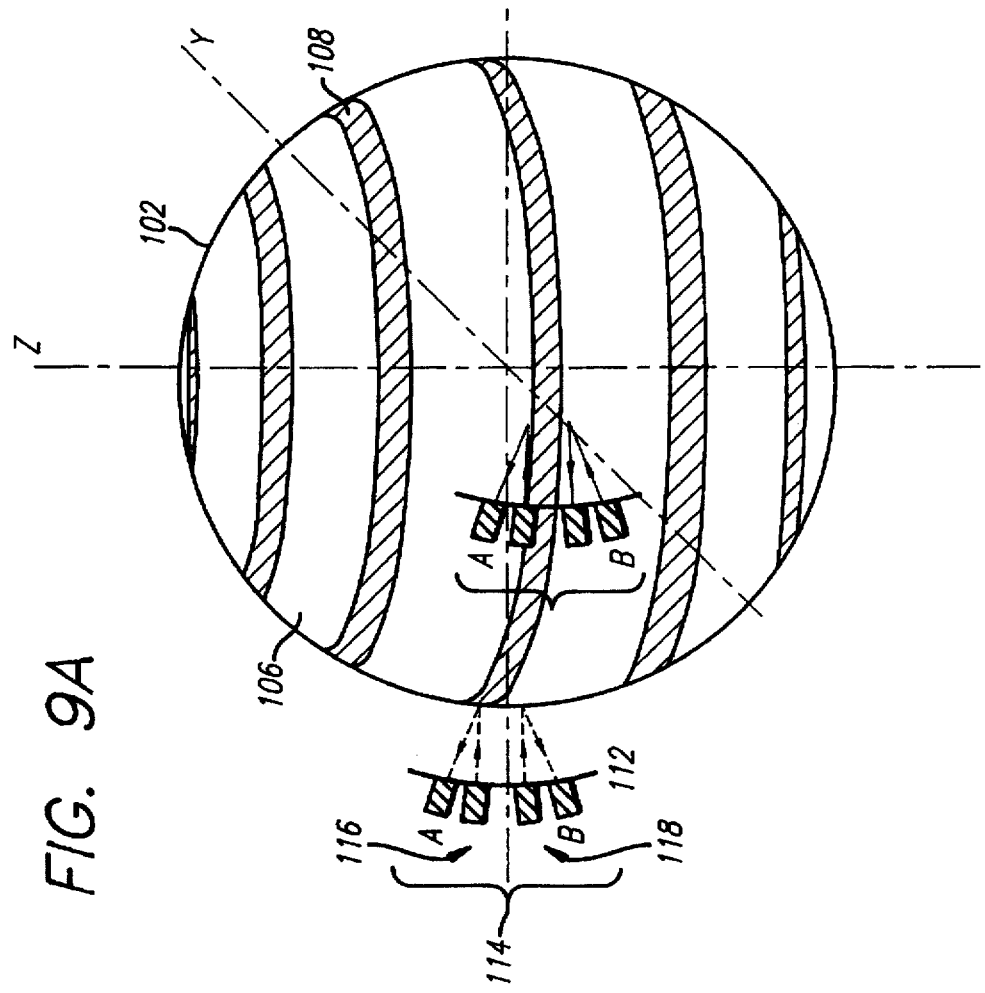
FIG. 9A is a perspective view of a suspended spherical ball for use in another embodiment of the orientation sensor of the present invention.

In another embodiment of the present invention, shown in FIGS. 9A–9C, the orientation sensor 14 includes a spherical ball 102 that is suspended within a slightly larger transparent sphere 104 or shell using light oil or water 105 so that the ball can freely rotate within the transparent sphere. The surface of the suspended spherical ball has a mat black surface 106 overlayed with silvery reflective stripes 108 located at predetermined spacings on the spherical ball's surface. The mat black surface reflects almost no light whereas the silvery stripes strongly reflect light. A small weight 110, placed in the interior of the spherical ball, provides the gravity orientation.

The rotation of the spherical ball 102 about the x and y axes is detected by two optical units 112 and 114 lying in the y-z and x-z planes, respectively. Each optical unit includes two photodiode and photodetector units 116 and 118. One photodiode and photodetector unit 116 is associated with the electrical signal A and other unit 118 is associated with the electrical signal B. Accordingly, these units provide two electrical signals A and B on lines A and B having a lead-lag relationship between the electrical signals. As shown in FIG. 9C, a reflective stripe 108 below the A photodiode and photodetector unit 116 reflects light from the photodiode 120 to the photodetector 122 to provide one state of an electrical signal on the line A. However, the black surface 106 under the B photodiode and photodetector unit 118 fails to reflect light from the photodiode 124 to the photodetector 126, thus providing an opposite state of an electrical signal on the line B. Similar to the previous embodiments, when the transparent sphere rotates in a clockwise direction, voltage $V_A$ on line A will lead voltage $V_B$ on line B.

It will be noted that the previously mentioned orientation sensors have been based on gravity sensor that indicate rotation about an axis in a horizontal plane. However, such orientation sensors cannot indicate rotation about an axis parallel with the gravity vector. Thus, to indicate rotation about a vertical axis, another vector, besides the gravity vector, must be used.

Another embodiment of the present invention, shown in FIGS. 11A–11C, uses a magnetic vector provided by the earth's magnetic field to indicate rotation about a vertical axis. A permanent magnet 130 is located within the spherical ball 102' in the place of the weight 110. In addition, other orthogonal reflective stripes 132 are placed on the ball's surface. The areas 134, where the orthogonal stripes intersect, are painted mat black so that an electrical pulse is still generated in the unlikely event that the spherical ball is rotating so that, for one axis, light is being reflected off from a point that is traveling along a reflective stripe S1. In this situation, a pulse is still recorded as the point passes a reflective stripe S2. Thus, an orientation sensor 14 using the magnetic spherical ball 102' can indicate rotation about the vertical axis.

Since the mouse interface 80 has only two movement channel inputs, the third set of electrical signals, representing the spherical rotation about the vertical axis, must be multiplexed onto one of the movement channel inputs. Similarly, all three electrical signals can be multiplexed onto one movement channel input.

Figure 12:
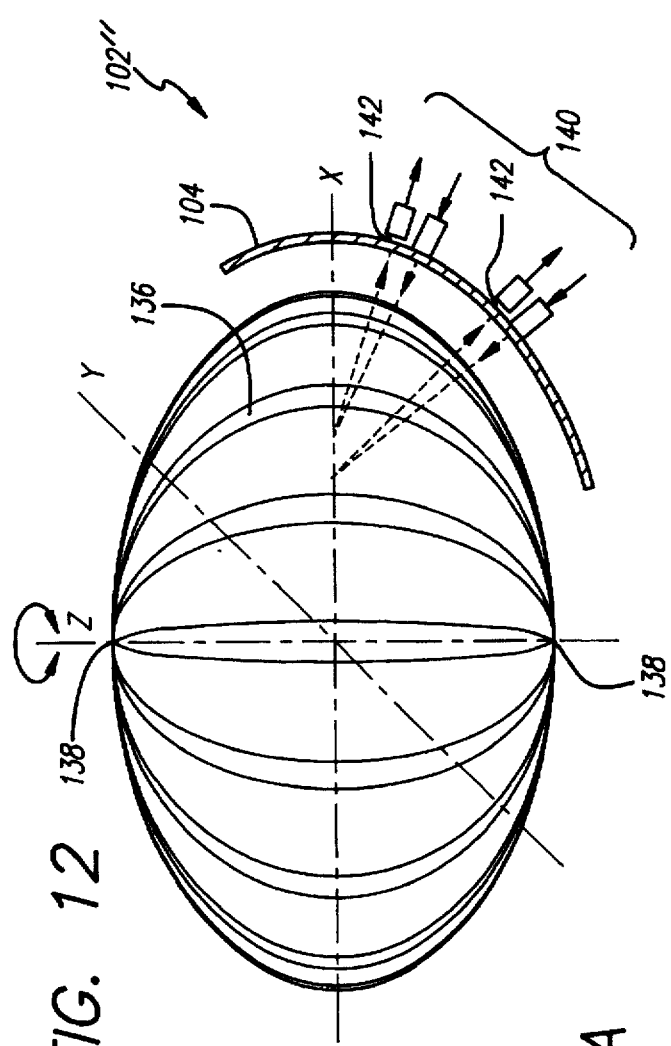
FIG. 12 is an alternative embodiment of the suspended spherical ball of FIG. 11A, and associated optical unit, having reflective stripes that provide uniform angular measurements.

Alternatively, as shown in FIG. 12, the reflective stripes 136 for any axis can originate from the axis' intersection 138 with the surface of the spherical ball 102". Thus, all pulses would uniformly indicate rotation regardless of the spherical ball's rotation. If the orientation sensor 14 is to be used for tri-axial orientation sensing, then the silvery stripes are replaced with reflective stripes of three different colors. Each color represents a different axis. Further, the corresponding photodiode and photodetector unit 140 has a light filters 142 so that the unit responds only to light associated with only one specific stripe color. Further, areas of intersection are colored to provide continuity for the respective colored stripes. For example, blue and yellow stripes will intersect with green areas.

Figure 13B:
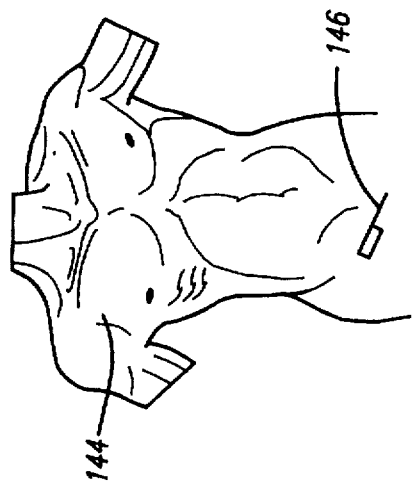
FIG. 13A and 13B are schematic diagrams each showing a special cursor placed on an image of a body for indicating the orientation of a recorded ultrasonic image.
Figure 13A:
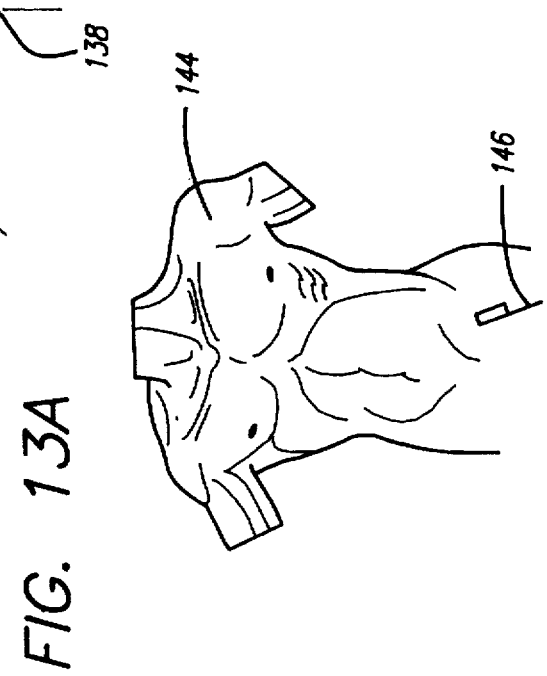

Shown in FIGS. 13A and 13B are body patterns 144 commonly used in ultrasonic imaging in the abdominal area. A transducer symbol 146 is placed on the pattern's abdominal area from which the displayed ultrasound image originates for future reference. Accordingly, in one embodiment of the present invention, the transducer symbol is oriented in response to the electrical signals received from the orientation sensor, thus relieving the operator of the task of manually changing the transducer symbol for inclusion on the recorded ultrasonic image.

Figure 14A:
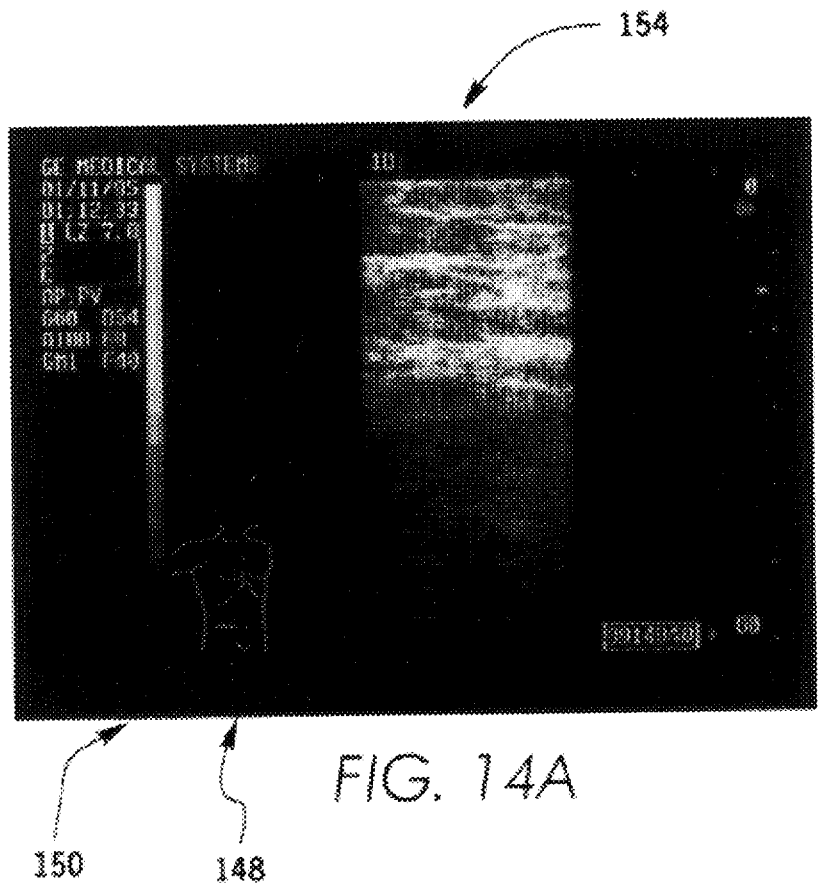
FIG. 14A is a recorded ultrasonic image further including a schematic diagram of a body torso overlayed with a special cursor that indicates the orientation of the imaging plane.
Figure 14B:
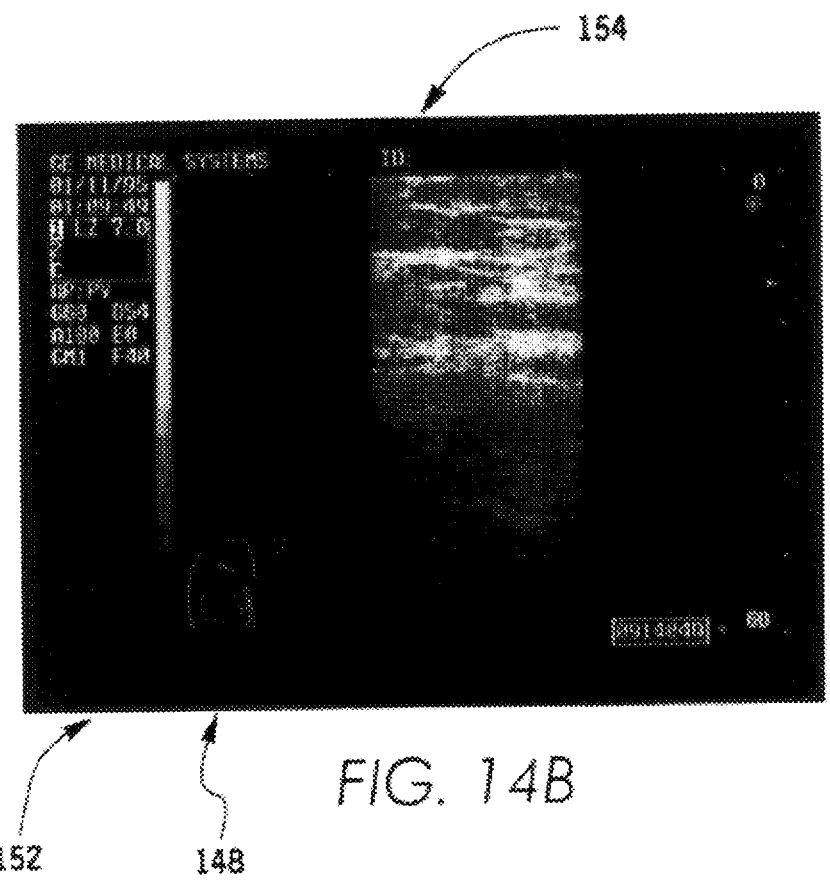
FIG. 14B is a recorded ultrasonic image further including a schematic diagram of an organ overlayed with a special cursor that indicates the orientation of the image plane.

Further, as shown in FIGS. 14A and 14B, the sensing and display apparatus 10 of the present invention may be integrated with an ultrasonic imaging processor, so that a special cursor 148 representing the imaging plane is automatically oriented on a small figure of the body 150 or organ 152 being imaged, with an ultrasonic image 154, for future reference.

Figure 15:
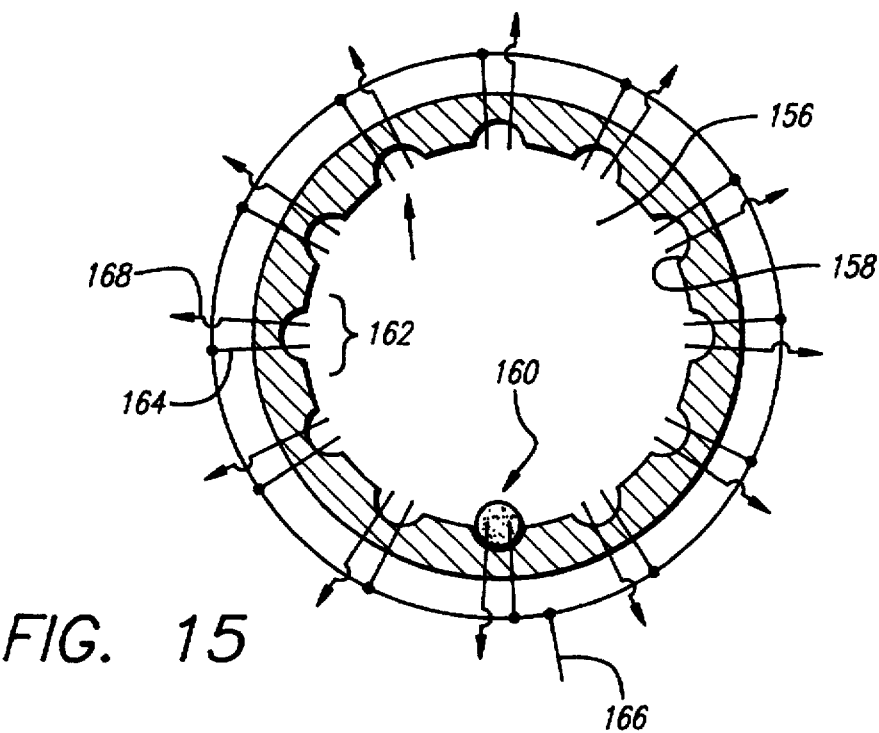
FIG. 15 is an alternative embodiment of an orientation sensor of the present invention, that includes a hollow sphere having sensing electrodes within indents.

In a final embodiment of the present invention, shown in FIG. 15, the orientation sensor 14 is a hollow sphere 156 having many evenly distributed shallow indents 158 (exaggerated in the drawing). As the sensor rotates, a mercury droplet 160 (or steel ball) temporary settles in an indent until the rotation is sufficient to move it to an adjacent indent. In each indent is an electrode pair 162. One electrode 164 is connected to a common terminal 166 and remaining electrodes are each connected to its own individual output line 168. The output line associated with the electrode that is connected to the common terminal by the mercury droplet indicates the orientation of the sensor.

Although the foregoing discloses the presently preferred embodiments of the present invention, it is understood that those skilled in the art may make various changes to the preferred embodiment shown without departing from the scope of the invention. The invention is defined only by the following claims.

We claim:

1. An apparatus for providing an indication of an imaging plane of an ultrasonic transducer, comprising:

a sensor that provides an electronic signal representing a spatial orientation of the imaging plane of the ultrasonic transducer;

a display that displays the imaging plane and a symbol indicating the spatial orientation of the imaging plane; and a processor, associated with the sensor and the display, that processes the electronic signal and generates a signal representing the spatial orientation that causes the display to manipulate the symbol.

2. Apparatus for providing an indication of an imaging plane as defined in claim 1, further comprising a laparoscopic instrument having an elongated tube with a tip section that can be articulated at various angles and directions with respect to the elongated tube; and the sensor and the ultrasonic sensor are located in the tip section.

3. An apparatus for providing an indication of an imaging plane as defined in claim 1, wherein said symbol on said display comprises:

a stationary element representing a portion of said ultrasonic transducer; and a dynamic element indicating relative orientation of an articulated tip of said ultrasonic transducer and/or said imaging plane thereof.

4. An apparatus for providing an indication of an imaging plane as defined in claim 3, wherein said dynamic element comprises a special cursor representing said imaging plane.

5. An apparatus for providing an indication of an imaging plane as defined in claim 1, wherein said display is divided to provide a plurality of views, said views being of different dimensional representations.

6. An apparatus for providing an indication of an imaging plane as defined in claim 1, wherein said processor processes a set of imaging planes and combines corresponding ultrasound images based on their respective electronic signals to provide a three-dimensional image on said display.

7. An apparatus for providing an indication of an imaging plane as defined in claim 1, wherein the sensor comprises:

a hollow sphere whose inner surface provides uniformly spaced apart indentations adapted to receive a gravity indicator, a plurality of electrode units, each of which is situated in a distinct one of said indentations; and a common electrode;

wherein the gravity indicator freely moves within the sphere so that the gravity indicator gravitates toward an indentation of the sphere with the lowest gravity potential to provide electrical contact between the common electrode and the electrode units as the gravity indicator settles in the respective indentation so that the sensor provides the signal.

8. An apparatus for providing an indication of an imaging plane, comprising:

a sensor that provides an orientation signal representing a spatial orientation of the imaging plane of the ultrasonic transducer, wherein the sensor comprises:

first and second sensing toroids, each toroid including a plurality of electrode units uniformly spaced apart around the toroid, each unit including at least two electrodes;

a common electrode;

a gravity indicator that freely moves within the toroid so that the gravity indicator gravitates toward the portion of the toroid with the lowest gravity potential as the toroid rotates, wherein the gravity indicator, as it moves to the toroid's lowest gravity potential, provides electrical contact between the common electrode and the electrode units to generate electrical pulses, wherein a phase lead/lag relationship between electrical pulses of an electrode unit indicates the direction of rotation and number of electrical pulses from different electrode units indicates the rotation angle.

9. An apparatus as defined in claim 8, wherein the gravity indicator is a droplet of mercury metal.

10. An apparatus as defined in claim 8, wherein the gravity indicator is made of a nontoxic material.

11. A sensor for providing an orientation signal compatible with a computer input, comprising:

an indicator responsive to gravity;

a plurality of probe pairs that monitor the movement of the indicator about an axis, said probe pairs being configured such that said indicator interacts distinctly with each of said probe pairs to provide pulses, wherein a phase lead/lag relationship between the pulses of a probe pair indicates a direction of rotation and number of pulses from different probe pairs indicates a rotation angle.

12. A sensor as defined in claim 11, wherein:

the indicator consists of a conductive metal; and each probe of the plurality of probe pairs includes an electrode that provides a respective pulse when in electrical contact with the conductive indicator.

13. A sensor for providing an orientation signal compatible with a computer mouse input port, comprising:
   a indicator responsive to gravity;
   a plurality of probe pairs that monitor the movement of the indicator about an axis, each probe pair providing first and second pulse signals, the timing between the pulse signals providing an indication of the angle and direction of the indicator's movement, wherein:
   the indicator has a reflective surface; and
   each probe of the plurality of probe pairs includes an optical detector that provides the respective pulse based on light reflected from the indicator's reflective surface.

14. An apparatus for providing an indication of an imaging plane of an ultrasonic transducer, comprising:
   a gravitational sensor that provides an electronic orientation signal representing a spatial orientation of the imaging plane of the ultrasonic transducer;
   a display that provides a visual representation of the imaging plane; and
   a processor, associated with the gravitational sensor and the display, that processes the electronic orientation signal and generates a display signal that causes the display to provide the visual representation of the imaging plane, wherein:
   the orientation signal provided by the gravitational sensor indicates the orientation of the ultrasonic sensor about a pair of axes in a horizontal plane; and
   the gravitational sensor further comprises a magnetic sensor, responsive to the earth's magnetic field, that provides an orientation signal that indicates the orientation of the ultrasonic sensor about a vertical axis.

15. Apparatus for providing an indication of an imaging plane as defined in claim 14, wherein:
   the orientation signal provided by the gravitational sensor indicates the orientation of the imaging plane with respect to a pair of axis in a horizontal plane; and
   the gravitational sensor further comprises a magnetic sensor, responsive to the earth's magnetic field, that provides an orientation signal that indicates the orientation of the imaging plane with respect to a vertical axis.

16. An apparatus for providing an indication of an imaging plane of an ultrasonic transducer, comprising:
   a gravitational sensor that provides an electronic orientation signal representing a spatial orientation of the imaging plane of the ultrasonic transducer;
   a display that provides a visual representation of the imaging plane; and
   a processor, associated with the gravitational sensor and the display, that processes the electronic orientation signal and generates a display signal that causes the display to provide the visual representation of the imaging plane, wherein the gravitational sensor comprises:
   first and second sensing toroids, each toroid including
     an illumination fiber that directs illumination light towards the toroid's interior;
     a plurality of detection fiber units, spaced apart around the toroid, that provide electrical signals based on illumination light received by the detection fiber unit;
     a gravity indicator, having a reflective surface, that moves within the toroid so that the gravity indicator tends gravitates toward the portion of the toroid with the lowest gravity potential, wherein the gravity indicator, as it moves to the toroid's lowest gravity potential, provides an optical reflection of the illumination light to only one detection fiber unit such that the gravitational sensor provides the orientation signal.

17. An apparatus for providing an indication of an imaging plane of an ultrasonic transducer, comprising:
   a gravitational sensor that provides an electronic orientation signal representing a spatial orientation of the imaging plane of the ultrasonic transducer;
   a display that provides a visual representation of the imaging plane; and
   a processor, associated with the gravitational sensor and the display, that processes the electronic orientation signal and generates a display signal that causes the display to provide the visual representation of the imaging plane, wherein the gravitational sensor comprises:
   a relatively transparent sphere filled with a relatively transparent liquid;
   a ball suspended by the liquid within the transparent sphere such that the ball can freely rotate within the transparent sphere, the ball having a black outer surface overlaid with reflective stripes and having a weight, placed on the interior of the spherical ball such that the ball gravitates toward a predetermined orientation with respect to the direction of gravity,
   at least one optical unit that directs light at the ball and that is oriented so that the optical unit, responsive to the intensity of light reflected from the surface of the ball, generates the orientation signal.

18. Apparatus for ultrasonic imaging, comprising:
   a laparoscopic instrument having
     an elongated tube section, and
     a short tube section located at an end of the elongated tube, the short tube being configured to articulate at various angles and directions with respect to the elongated tube;
   an ultrasonic sensor, responsive to structures in an imaging plane, that is housed in the short tube section and that generates electrical signals associated with the structures in the imaging plane; and
   a sensor having a plurality of probe pairs for providing pulse signals representing a spatial orientation of the imaging plane, wherein a phase lead/lag relationship between the pulse signals of a probe pair indicates a direction of rotation and number of the pulse signals from different probe pairs indicates a rotation angle.

19. An apparatus for ultrasonic imaging, comprising:
   a laparoscopic instrument having
     an elongated tube section, and
     a short tube section located at an end of the elongated tube, the short tube being configured to articulate at various angles and directions with respect to the elongated tube;
   an ultrasonic sensor, responsive to structures in an imaging plane, that is housed in the short tube section and that generates electrical signals associated with the structures in the imaging plane; and
   an orientation sensor that provides a signal representing a spatial orientation of the imaging plane, wherein the orientation sensor comprises:
   first and second sensing toroids, each toroid including
     a plurality of electrode units uniformly spaced apart around the toroid, each unit including at least two electrodes;

a common electrode;

a gravity indicator that freely moves within the toroid so that the gravity indicator gravitates toward the portion of the toroid with the lowest gravity potential, wherein the gravity indicator, as it moves to the toroid's lowest gravity potential, provides electrical contact between the common electrode and the electrode units, said electrode units being configured such that said gravity indicator interacts distinctly with each of said electrode units in providing pulses, wherein a phase lead/lag relationship between the pulses of an electrode unit indicates a direction of rotation and number of pulses from different electrode units indicates a rotation angle.

20. An apparatus for ultrasonic imaging as defined in claim 19, wherein the gravity indicator is a droplet of mercury metal.

21. An apparatus for ultrasonic imaging, comprising:

a laparoscopic instrument having
  an elongated tube section, and
  a short tube section located at an end of the elongated tube, the short tube being configured to articulate at various angles and directions with respect to the elongated tube;
an ultrasonic sensor, responsive to structures in an imaging plane, that is housed in the short tube section and that generates electrical signals associated with the structures in the imaging plane; and
a sensor that provides an orientation signal representing a spatial orientation of the imaging plane, wherein the sensor comprises:
  a gravity indicator responsive to gravity;
  a plurality of probe pairs that monitor the movement of the gravity indicator about an axis, each of said probe pairs having a first probe and a second probe, said first probes of said plurality of probe pairs being connected to a first common node, said second probes of said plurality of probe pairs being connected to a second common node.

22. Apparatus for ultrasonic imaging, comprising:

a laparoscopic instrument having
  an elongated tube section, and
  a short tube section located at an end of the elongated tube, the short tube being configured to articulate at various angles and directions with respect to the elongated tube;
an ultrasonic sensor, responsive to structures in an imaging plane, that is housed in the short tube section and that generates electrical signals associated with the structures in the imaging plane; and
a gravitational sensor that provides an orientation signal representing a spatial orientation of the imaging plane, wherein:
  the orientation signal provided by the gravitational sensor indicates the orientation of the ultrasonic sensor about a pair of axis in a horizontal plane; and
  the gravitational sensor further comprises a magnetic sensor, responsive to the earth's magnetic field, that provides an orientation signal that indicates the orientation of the ultrasonic sensor about a vertical axis.

23. Apparatus for ultrasonic imaging, comprising:

a laparoscopic instrument having
  an elongated tube section, and
  a short tube section located at an end of the elongated tube, the short tube being configured to articulate at various angles and directions with respect to the elongated tube;
an ultrasonic sensor, responsive to structures in an imaging plane, that is housed in the short tube section and that generates electrical signals associated with the structures in the imaging plane; and
a gravitational sensor that provides an electrical orientation signal representing a spatial orientation of the imaging plane, wherein the gravitational sensor comprises:
  first and second sensing toroids, each toroid including
    an illumination fiber that directs illumination light towards the toroid's interior;
    a plurality of detection fiber units, spaced apart around the toroid, that provides electrical signals based on illumination light received by the detection fiber unit;
    a gravity indicator, having a reflective surface, that freely moves within the toroid so that the gravity indicator gravitates toward the portion of the toroid with the lowest gravity potential, wherein the gravity indicator, as it moves to the toroid's lowest gravity potential, provides an optical reflection of the illumination light to only one detection fiber unit such that the gravitational sensor provides the orientation signal.

24. Apparatus for ultrasonic imaging, comprising:

a laparoscopic instrument having
  an elongated tube section, and
  a short tube section located at an end of the elongated tube, the short tube being configured to articulate at various angles and directions with respect to the elongated tube;
an ultrasonic sensor, responsive to structures in an imaging plane, that is housed in the short tube section and that generates electrical signals associated with the structures in the imaging plane; and
a gravitational sensor that provides an electrical orientation signal representing a spatial orientation of the imaging plane, wherein the gravitational sensor comprises:
  a relatively transparent sphere filled with a relatively transparent liquid;
  a ball suspended by the liquid within the transparent sphere so that the ball can freely rotate within the transparent sphere, the ball having a black outer surface overlaid with reflective stripes and having a weight, placed on the interior of the spherical ball, that provides gravity orientation,
  at least one optical unit that directs light at the spherical ball and that is oriented so that the optical unit, responsive to the intensity of light reflected from the surface of the ball, generates the orientation signal.

25. Apparatus for providing an indication of an image plane as defined in claim 24, wherein:

the orientation signal provided by the gravitational sensor indicates the orientation of the ultrasonic sensor about a pair of axis in a horizontal plane; and
the gravitational sensor further comprises a magnetic sensor, responsive to the earth's magnetic field, that provides an orientation signal that indicates the orientation of the ultrasonic sensor about a vertical axis.

26. An apparatus for providing an indication of an imaging plane of an ultrasonic transducer, comprising:

a gravitational sensor that provides an electronic orientation signal representing a spatial orientation of the imaging plane of the ultrasonic transducer;

a display that provides a visual representation of the imaging plane; and a processor, associated with the gravitational sensor and the display, that processes the electronic orientation signal and generates a display signal that causes the display to provide the visual representation of the imaging plane, wherein said visual representation is divided to provide a plurality of views, said views being of different dimensional representations and wherein a first view is a three-dimensional representation, a second view is a two-dimensional representation.

27. An apparatus for providing an indication of an imaging plane as defined in claim 26, wherein said second view utilizes different colors to indicate orientation of said imaging plane in different coordinate planes.

28. An apparatus for providing an indication of an imaging plane of an ultrasonic transducer, comprising:

a gravitational sensor that provides an electronic orientation signal representing a spatial orientation of the imaging plane of the ultrasonic transducer;

a display that provides a visual representation of the imaging plane; and a processor, associated with the gravitational sensor and the display, that processes the electronic orientation signal and generates a display signal that causes the display to provide the visual representation of the imaging plane wherein said visual representation comprises:

a stationary element representing a portion of said ultrasonic transducer; and a dynamic element indicating relative position of an articulated tip of said ultrasonic transducer and/or said imaging plane thereof and wherein said dynamic element comprises a vector symbol representing an imaging direction.

* * * * *